(12) United States Patent
Domes et al.

(10) Patent No.: US 6,984,289 B2
(45) Date of Patent: Jan. 10, 2006

(54) PROCESS OF GENERATING O-XYLENE-AIR MIXTURES FOR THE PRODUCTION OF PHTHALIC ANHYDRIDE

(75) Inventors: Helmuth Domes, Obertshausen (DE); Thomas Gutermuth, Maintal (DE); Herbert Feisel, Hofheim (DE); Lutz Urban, Schmitten (DE)

(73) Assignee: MG Technologies AG, Frankfurt am Main (DE)

( * ) Notice: Subject to any disclaimer, the term of this patent is extended or adjusted under 35 U.S.C. 154(b) by 423 days.

(21) Appl. No.: 10/179,864

(22) Filed: Jun. 25, 2002

(65) Prior Publication Data

US 2003/0089460 A1 May 15, 2003

(30) Foreign Application Priority Data

Jul. 5, 2001 (DE) .................................. 101 32 627

(51) Int. Cl.
*B01D 1/14* (2006.01)
*C07D 307/89* (2006.01)

(52) U.S. Cl. .................... 159/16.1; 159/16.3; 159/47.1; 549/248; 549/250

(58) Field of Classification Search ................ 159/16.1, 159/16.3, 47.1, 4.01, DIG. 10; 549/248, 250; 203/49; 422/129
See application file for complete search history.

(56) References Cited

U.S. PATENT DOCUMENTS

| 3,480,408 A | * | 11/1969 | Lacroix | 422/140 |
| 3,535,345 A | * | 10/1970 | Egbert | 549/249 |
| 4,119,645 A | * | 10/1978 | Auroy et al. | 549/248 |
| 4,169,098 A | * | 9/1979 | Hellmer et al. | 549/248 |

FOREIGN PATENT DOCUMENTS

| DE | 2839831 | * | 3/1980 |
| EP | 0483645 | * | 5/1992 |
| GB | 1063152 | * | 3/1967 |

* cited by examiner

*Primary Examiner*—Virginia Manoharan
(74) *Attorney, Agent, or Firm*—Norris McLaughlin & Marcus PA

(57) ABSTRACT

Process for generating a homogeneous gas mixture of o-xylene and air for the production of phthalic anhydride wherein o-xylene is completely evaporated in the absence of oxygen, superheated and then mixed with air and supplied to a phthalic anhydride reactor.

6 Claims, 3 Drawing Sheets

PROCESS OF GENERATING O-XYLENE-AIR MIXTURES FOR THE PRODUCTION OF PHTHALIC ANHYDRIDE

DESCRIPTION

This invention relates to a process of generating a homogeneous gas mixture (feed gas) from ortho-xylene (o-xylene) and air, which is the basis for the production of phthalic anhydride (PA) by gas-phase oxidation in the so-called PA-process.

The generation of feed gas for the PA process operated with o-xylene as feedstock has so far been performed as follows:

The process air is sucked in from the surroundings by means of a blower, filtered, and subsequently compressed to a pressure level which allows the conveyance of the air stream through the process gas strand of the PA plant. In a heat exchanger disposed behind the blower, this process air stream is raised in its temperature level. Parallel thereto, liquid o-xylene from a storage tank is brought to a certain preliminary pressure by means of a pump and passed through a preheater. In a so-called evaporator, the preheated o-xylene is injected into the air stream in liquid form parallel to the air flow by means of a nozzle system. The fine o-xylene droplets completely evaporate in the air stream, and finally a levelling of the concentration and temperature distribution in the gas stream is achieved by means of a homogenization stage (e g. a static mixer). This feed gas subsequently enters the tubular reactor filled with catalyst, where a partial oxidation of o-xylene and atmospheric oxygen to form phthalic anhydride takes place.

For decades, the above-described process principle for the generation of feed gas has successfully been used in the PA process, but with the successive introduction of higher o-xylene loads in the air stream (>80 g o-xylene per $Nm^3$ air) has also shown potential weaknesses with regard to the explosion safety of the feed gas part of the PA plant, which will be explained below.

The lower explosion limit of a gaseous mixture of o-xylene and air is about 44 $g/Nm^3$. It was found out that the minimum energy required for igniting the mixture is greatly decreased with increasing o-xylene load, and therefore an increased sensibility with regard to the possibility of an explosion does exist. To a great extent, the economy of the PA process depends on the load of o-xylene per $Nm^3$ air. It is a basic requirement that plants with a capacity of 80 g o-xylene/$Nm^3$ air to 120 g o-xylene/$Nm^3$ air must be operated safely With respect to the possible causes of an ignition in the feed gas part of a PA plant, especially when using the above-described process of generating feed gas, the following should be noted:

When atomizing the liquid o-xylene in the spray nozzles, static electricity is built up in the o-xylene droplet itself, whose discharge via installations in the evaporator can lead to a spark which in turn can be the cause of an explosion.

The deposition of evaporation residues from the evaporated o-xylene on internal fittings of the evaporator can lead to the build-up of solid layers, which by chemical reaction with oxygen from the process air can form pyrophoric substances which in turn represent potential ignition sources for an explosion.

DE-A-2839831 describes a process of producing a gas mixture for the oxidation of naphthalene, in which the naphthalene evaporates in the absence of oxygen, the evaporated naphthalene is mixed with oxygen, and the mixing ratio of naphthalene to oxygen is adjusted by measuring the flow rate. In this process, which is performed by using naphthalene, a capacity of 40 g naphthalene/$Nm^3$ air is achieved.

EP-B-0483645 desribes a process of generating a feed gas mixture from naphthalene, o-xylene and air. Ortho-xylene is first of all evaporated in the absence of oxygen and is subsequently passed through liquid naphthalene, so that the o-xylene vapors are saturated with naphthalene. This mixture is then supplied to the process air. A contact of the naphthalene to be evaporated with atmospheric oxygen is avoided, which would otherwise lead to the continuous formation of tarry by-products in the naphthalene evaporator and would result in an increased necessity for cleaning the same. In this process, the capacity is limited to 100 g hydrocarbons/$Nm^3$ air.

It is the object underlying the invention to create a process of producing o-xylene-air mixtures for the production of phthalic anhydride, by means of which a load of 80 g o-xylene per $Nm^3$ air to 120 g o-xylene per $Nm^3$ air can be achieved.

In accordance with the invention, this object is solved in that o-xylene is completely evaporated in the absence of oxygen, is superheated thereafter and is then mixed with oxygen-containing air, and this mixture is supplied to the PA reactor.

To obtain a homogeneous premix of the two components, a gas-gas mixing means designed as sparger system is provided at the point where the o-xylene vapor is admixed to the process air. A subsequently provided static mixing means ensures the complete homogenization of the mixture.

As evaporator, a kettle-type evaporator or a natural-circulation evaporator may be used. The kettle-type evaporator represents the technically simpler and thus less expensive solution and therefore is preferred in general. If the o-xylene has high contents of by-products with styrene or cumol, deposits may be formed at the evaporator surfaces, which deposits impede the transfer of heat; this can be avoided by using a circulating evaporator, as the same has higher flow rates in the vicinity of the evaporator surfaces.

The o-xylene must be evaporated at a temperature of at least 175° C., which corresponds to a vapor pressure of 2.3 bar absolute. This ensures a sufficient pressure gradient for admixing the o-xylene to the process air, which at the point where the vaporous o-xylene is admixed has a pressure of about 1.5 bar absolute. For the practical realization of the plant, a temperature of 180° C. to 205° C. is chosen for the evaporation of o-xylene, which corresponds to vapor pressures of 2 4 bar to 4 bar absolute.

An important requirement of the evaporation system consists in that the flow of o-xylene vapor remains constant, as the catalyst in the PA reactor may be damaged in the case of fluctuations of the o-xylene load in the air stream within short operating periods; this is true in particular for high o-xylene loads. The supply of vapor to the o-xylene evaporator normally fluctuates within certain limits, which involves fluctuations of the o-xylene stream to be evaporated. This can at least largely be avoided by using a sufficiently dimensioned steam accumulator for supplying steam to the o-xylene evaporator. Moreover, fluctuations are decreased with increasing pressure in the o-xylene evaporator.

The embodiments of the process will now be explained by way of example with reference to the drawing, in which.

Figure 1:
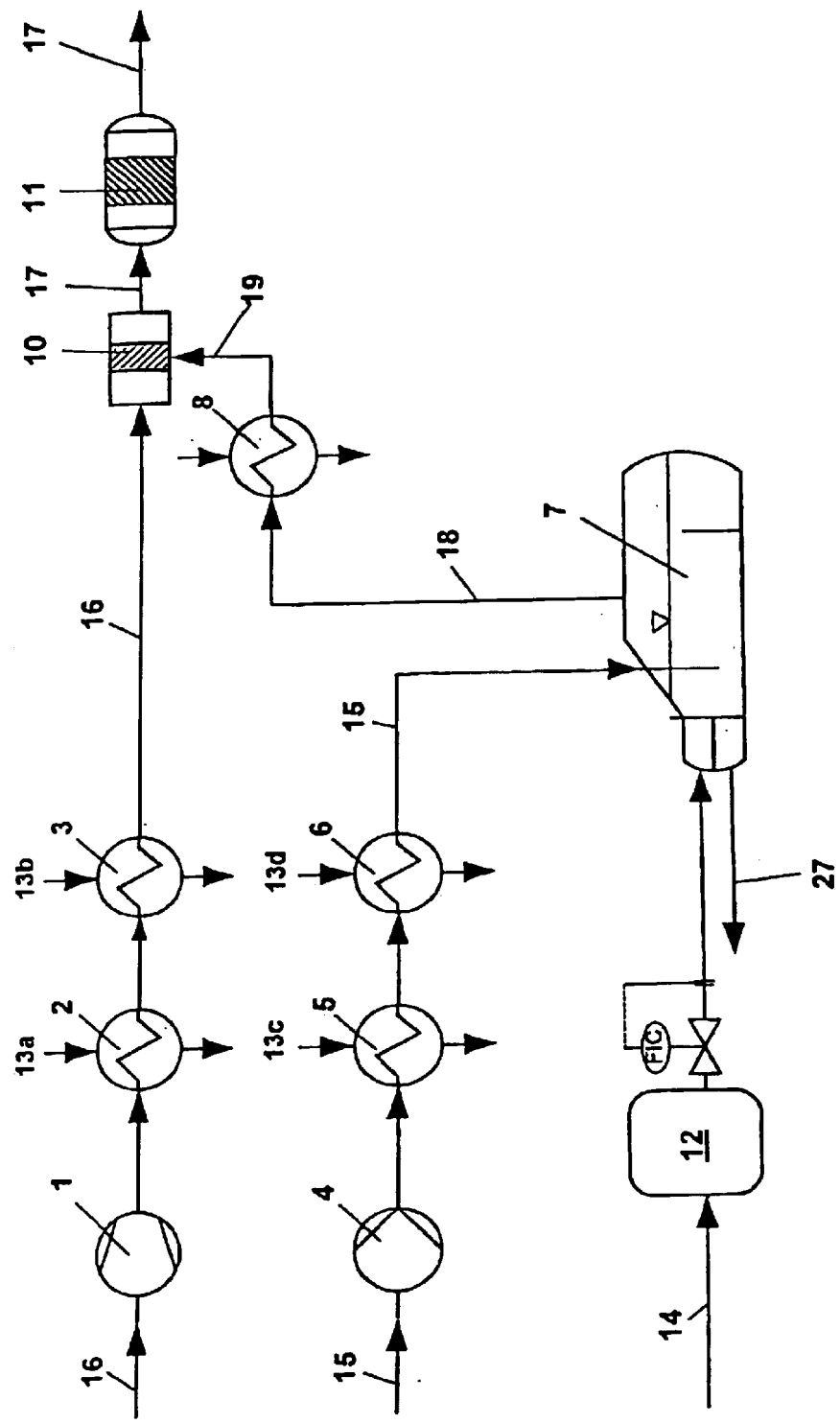
FIG. 1 shows a flow diagram of the process with a kettle-type evaporator.

As shown in FIG. 1, o-xylene (15) is supplied by means of the o-xylene pump (4) from a storage tank through the two o-xylene preheaters (5) and (6), where the o-xylene is heated to 180° C. by means of steam (13c, 13d). On the pressure side, the o-xylene pump (4) provides an absolute pressure of 2.5 bar. Subsequently, the liquid o-xylene (15) flows into the kettle-type evaporator (7). In its interior, this kettle-type evaporator has steam-heated tubular coils, which are not represented here. The o-xylene (15) is evaporated at absolute pressures of 2.4 bar to 4 bar, which corresponds to an evaporation temperature of 180° C. to 205° C. As heating medium, saturated steam (14) between 18 and 30 bar is used, which with a temperature of 210° C. at 18 bar or 234° C. at 30 bar has enough temperature difference with respect to the medium to be evaporated. For keeping constant the saturated steam flow to the o-xylene evaporator (7), a steam accumulator (12) is used, which is positioned between the steam supply from the steam network and the o-xylene evaporator (7).

The o-xylene vapor (18) thus generated is withdrawn from the vapor space of the kettle-type evaporator (7) and passed through a superheater (8), which superheats the o-xylene vapor (18) by 10° C., in order to avoid a condensation of the vapor. Excess condensate (27) is withdrawn from the evaporator (7). Avoiding the condensation of o-xylene vapor is of decisive importance for controlling the flow rate of o-xylene, as the same is effected by measuring the flow rate of the o-xylene vapor, and the condensation of o-xylene vapor would lead to fluctuations of the o-xylene load in the process air stream. Finally, the superheated o-xylene vapor (19) is mixed with the process air (16) in a special mixing means (10), which process air is supplied by the process air blower (1) through the two-stage preheaters (2) and (3) towards the reactor. The mixing means (10) is designed such that at the admixing point there is already achieved a good mixing of the superheated o-xylene vapor (19) with the process air (16). This is effected by means of sparger rings, which distribute the o-xylene vapor over the entire conduit cross-section of the process air line. In the preheaters (2, 3), the process air (16) is heated to about 150° C. The combined feed gas stream (17) passes through a static mixer (11) for the purpose of homogenizing concentration and temperature, which is of extreme importance for the safe and efficient operation of the oxidation reactor in these high load ranges. Premixing the superheated o-xylene vapor (19) as homogeneously as possible in the mixing means (10) (see also FIG. 3) is necessary, because the static mixer (11) can only mix with a fixed efficiency and therefore already requires a thoroughly homogenized mixture at its inlet, in order to be able to ensure the required mixing quality for the reactor.

Figure 2:
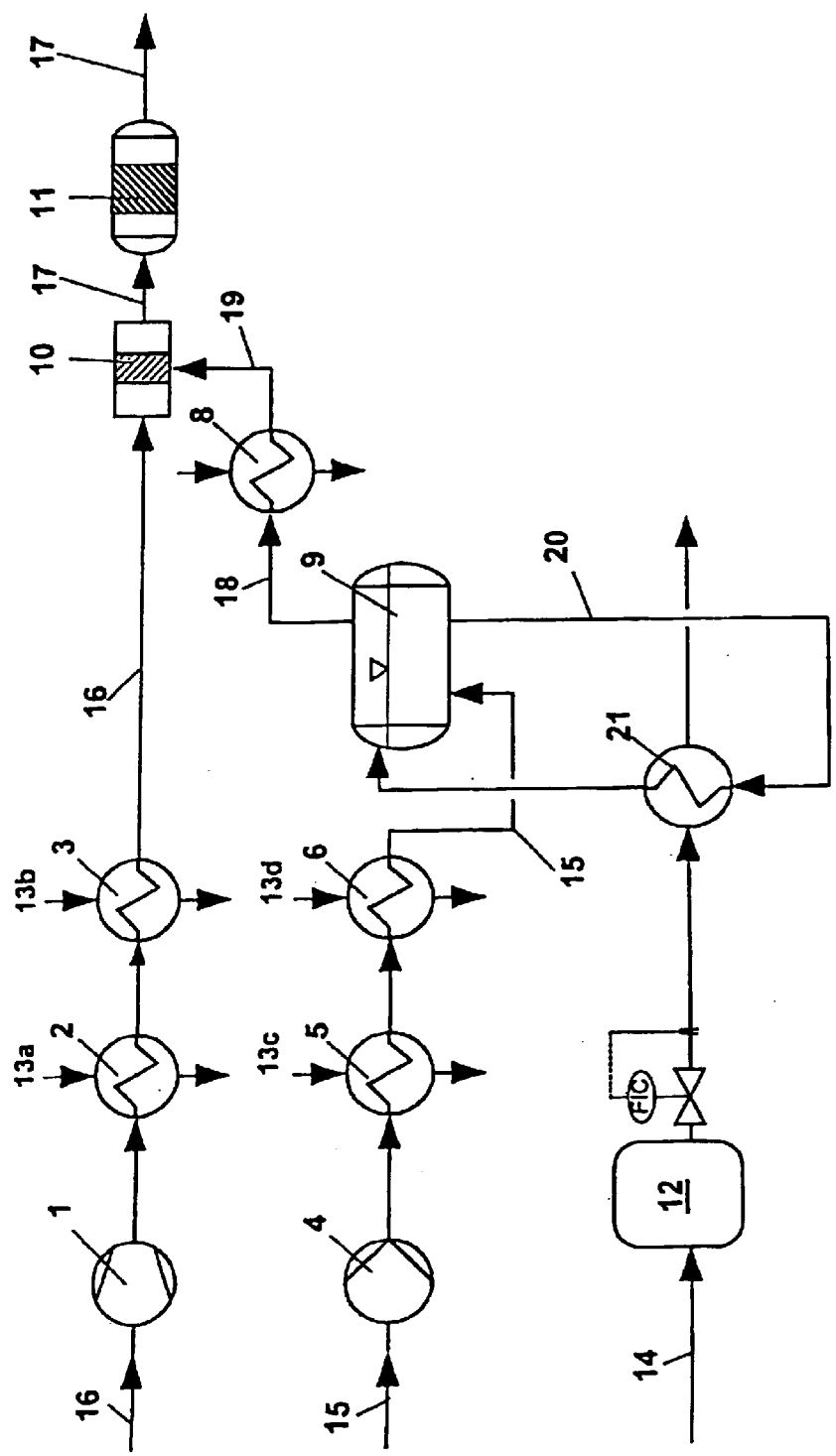
FIG. 2 shows the evaporation of o-xylene with a natural-circulation evaporator.

Instead of evaporating the o-xylene in a kettle-type evaporator, a natural circulation can be used as evaporation principle, as is represented in FIG. 2:

Upon preheating (5, 6), the o-xylene (15) gets into the o-xylene vapor drum (9). This o-xylene vapor drum (9) is fed by a natural circulation.

Through the downpipe (20), the boiling o-xylene (15) gets into a steam-heated evaporator (21), which operates as reboiler. Part of the o-xylene flowing through the same is evaporated at absolute pressures of about 2.4 to 4 bar and is then recirculated to the o-xylene vapor drum (9) by the natural circulation. From the vapor space, the vapors get into the superheater (8), where the o-xylene vapor (18) is superheated by 10° C., in order to avoid a condensation of the vapor, as described above. The further process is identical with the process described in FIG. 1.

Figure 3:
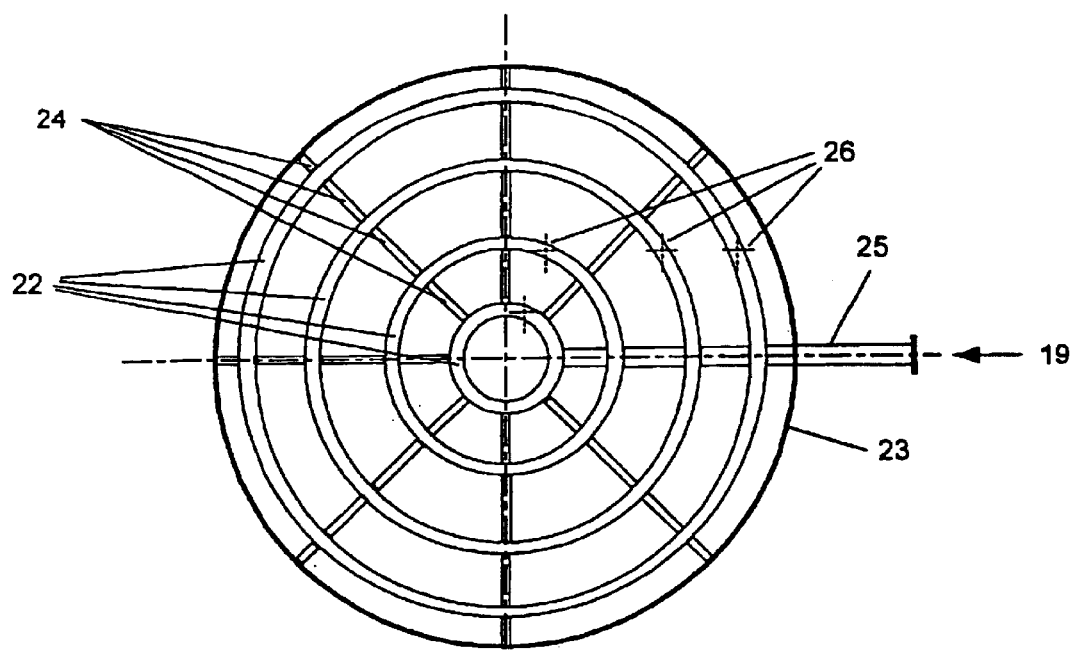
FIG. 3 shows a sparger ring system.

FIG. 3 shows a sparger ring system, by means of which the superheated o-xylene vapor (19) is mixed with the process air. A plurality of rings (22) are concentrically arranged inside the process air conduit (23). The rings (22) consist of bent and welded tubes. The distance between the rings (22) is defined by radial retaining sheets (24). Via a conduit (25), pressurized superheated o-xylene vapor (19) is introduced into all rings. The rings have a plurality of outlet openings (26) uniformly distributed over the periphery, through which the o-xylene vapor escapes and mixes with the process air.

EXAMPLE

For a PA plant with an annual capacity of 50,000 tons per year, the evaporation of o-xylene is performed according to the aforementioned principle, the plant operating 8000 h per year. The o-xylene has a purity of 98%. Since the plant operates with at load of 100 g o-xylene per $Nm^3$ air and the plant achieves a yield of 112% (kg produced pure PA per kg o-xylene used), an o-xylene stream of 50,000 t/a PA×1.12/8000/0.98=7143 kg o-xylene/h is required.

The air flow which the plant requires for oxidation is 71430 $Nm^3$/h.

The o-xylene pump supplies the o-xylene stream (20° C., atmospheric pressure), which at the pump outlet has a pressure of 1.8 bar and a temperature of 40° C. In the first heat exchanger operated with low-pressure steam of 2.5 bar, the o-xylene reaches a temperature of 135° C. In the second heat exchanger heated with 18 bar, the o-xylene stream is heated to 175° C. When entering the evaporator, the o-xylene has a pressure of 1.4 bar, if the heat exchangers and the conduits have a pressure loss of 0.4 bar.

The steam consumptions of the two preheaters are as follows:

1st preheater:

Heat flow: 7143 kg/h/3600 s/h×2.1 kJ/kg K×(135° C.−40° C.)=396 kW

Steam requirement: 396 kW/2153 kJ/kg×3600 s/h=662 kg/h (2.5 bar)

2nd preheater:

Heat flow: 7143 kg/h/3600 s/h×2.1 kJ/kg K×(175°−135° C.)=167 kW

Steam requirement: 167 kW/1900 kJ/kg K×3600 s/h=316 kg/h (18 bar)

The evaporator must evaporate 7143 kg o-xylene per hour. This requires a heat flow of: 7143 kg/h/3600 s/h×[315 kJ/kg+(180° C.−175° C.)×2.15 kJ/kg K]=1365 kW, which requires an amount of heating steam (18 bar) of 1365 kW/1900 kJ/kg×3600 s/h=2586 kg/h.

In the case of the natural-circulation evaporator system, 7143 kg/h/0.15=47620 kg/h o-xylene circulate in the evaporator circuit.

The o-xylene vapors escaping from the vapor drum are heated in the superheater by 10 K, so that they have a temperature of 190° C. at the superheater outlet.

The superheater requires a thermal output of 7143 kg/h/3600 s/h×1.9 kJ/kg K×(190° C.−180° C.)=38 kW, which corresponds to an amount of heating steam of 38 kW/1900 kJ/kg×3600 s/h=72 kg/h (18 bar).

At the outlet of the evaporator, the superheated o-xylene vapors have a pressure of 1.3 bar. These vapors are subsequently expanded into the process air stream, whose pressure is about 0.5 bar at this point.

We claim:

1. A process for producing an o-xylene-air mixture for the production of phthalic anhydride, wherein o-xylene is completely evaporated in the absence of oxygen, superheated and then mixed with air; and the mixture supplied to a phthalic anhydride reactor.

2. The process of claim 1, wherein said evaporation is accomplished by heating the o-xylene in an evaporator.

3. The process of claim 2, wherein said evaporator is heated with steam from a steam accumulator.

4. The process of claim 2, wherein said evaporator is a natural-circulation evaporator or a kettle evaporator.

5. The process of claim 1, wherein the said o-xylene is mixed with said air in the amount of from 80 to 120 g o-xylene/Nm$^3$ of air.

6. The process of claim 1, wherein said o-xylene and said air are mixed by a sparger ring mixer.

* * * * *

UNITED STATES PATENT AND TRADEMARK OFFICE
CERTIFICATE OF CORRECTION

PATENT NO.    : 6,984,289 B2
DATED         : January 10, 2006
INVENTOR(S)   : Domes et al.

It is certified that error appears in the above-identified patent and that said Letters Patent is hereby corrected as shown below:

Title page,
Item [*] Notice, should read -- Subject to any disclaimer, the term......by 455 days --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,984,289 B2  Page 1 of 1
APPLICATION NO. : 10/179864
DATED : January 10, 2006
INVENTOR(S) : Domes et al.

It is certified that error appears in the above-identified patent and that said Letters Patent is hereby corrected as shown below:

Column 2, Line 50, "of 2 4 bar" should read -- of 2.4 bar --

Column 5, Line 7, "with air; and" should read -- with air, and --

Signed and Sealed this

Fifteenth Day of April, 2008

JON W. DUDAS
*Director of the United States Patent and Trademark Office*